United States Patent [19]

Kondo et al.

[11] Patent Number: 4,647,693
[45] Date of Patent: Mar. 3, 1987

[54] ANTIBIOTICS DO-248-A AND B AND PROCESS FOR PREPARING THE SAME

[75] Inventors: Eiji Kondo; Yoshimi Kawamura; Takao Konishi; Koichi Matsumoto; Junichi Shoji, all of Osaka, Japan

[73] Assignee: Shionogi & Co., Ltd., Osaka, Japan

[21] Appl. No.: 719,737

[22] Filed: Apr. 3, 1985

[30] Foreign Application Priority Data

Apr. 16, 1984 [JP] Japan .................... 59-77372

[51] Int. Cl.$^4$ ........................ C07C 101/34
[52] U.S. Cl. .................... 562/439; 435/106; 514/565
[58] Field of Search ............ 562/439, 448; 435/106; 514/565

[56] References Cited

U.S. PATENT DOCUMENTS 3,994,965  11/1976  Nakanishi .................... 562/439

FOREIGN PATENT DOCUMENTS 59-144717  8/1984  Japan ...................... 562/439

Primary Examiner—James H. Reamer
Attorney, Agent, or Firm—Wenderoth, Lind & Ponack

[57] ABSTRACT

Antibiotics DO-248-A and DO-248-B of the following Formula I:

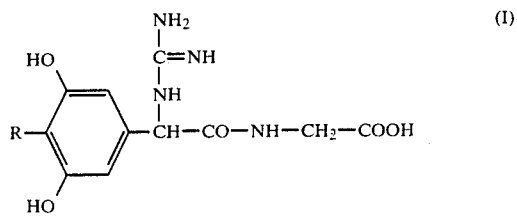

wherein R is ethyl or isopropyl, have antibacterial activity against acid-fast bacteria. DO-248-A, DO-248-B, or their pharmaceutically acceptable salts are, as an active ingredient of anti-fast-acid drugs, orally or parenterally administered to human beings or animal. DO-248-A and DO-248-B are prepared by incubating an antibiotic DO-248-A- and/or DO-248-B-producing microorganism belonging to genus Streptoverticillium in a medium and recovering antibiotic DO-248-A and/or DO-248-B from the culture broth.

3 Claims, 8 Drawing Figures

ANTIBIOTICS DO-248-A AND B AND PROCESS FOR PREPARING THE SAME

BACKGROUND OF THE INVENTION (1) Field of the Invention

This invention relates to antibiotics DO-248-A and DO-248-B of the following Formula I:

wherein R is ethyl or isopropyl,
and their pharmaceutically acceptable salts. Further it relates to a process for preparing these antibiotics and to anti-acid-fast organism compositions containing as an active ingredient these antibiotics and/or their pharmaceutically acceptable salts.

(2) Description of the Prior Art

Antibiotics have long been clinically used as an antitubercle drug and especially aminoglycosides such as streptomycin and kanamycin and semisynthetic macrolides such as rifampicin are generally used in combined drugs with other synthetic anti-tubercle drugs. Generally, it is hard to prevent occurrence of resistant microorganisms where an antibiotic has long been administered and it is a present problem that such resistant microorganisms have been occurred against the anti-tubercle drugs as above mentioned.

Though antibiotic pheganomycins have been known as antibiotics having α-guanidino-3,5-dihydroxyphenyl acetic acid residue {Proceeding of the 15th Symposium on Peptide Chemistry, 121 (1977)}, DO-248-A and DO-248-B are glycin derivatives and have a distinctly different chemical structure from pheganomycins which are hexa- or heptapeptide derivatives.

SUMMARY

Antibiotics DO-248-A and DO-248-B of this invention have antibacterial activity against acid-fast bacteria and kanamycin- and rifampicin-resistant bacteria and are more active against the pathogenic bacterium of atypical fast-acid bacterium disease than kanamycin. DO-248-A, DO-248-B, or their pharmaceutically acceptable salts are, as an active ingredient of anti-fast-acid drugs, orally or parenterally administered to human beings or animal. Antibiotics DO-248-A and DO-248-B are prepared by incubating an antibiotic DO-248-A-and/or DO-248-B-producing microorganisms belonging to the genus Streptoverticillium in a medium and recovering antibiotic DO-248-A and/or DO-248-B from the culture broth.

DETAILED DESCRIPTION OF THE INVENTION

The physicochemical properties of the antibiotics DO-248-A and DO-248-B of this invention are as follows.

(1)

DO-248-A

① Elemental analysis: Calcd. (%); for $C_{14}H_{20}N_4O_5.2H_2O$, C 46.66, H 6.71, N 15.58. Found (%); C 47.01, H 6.15, N 15.44.

② Molecular weight (by secondary ion mass spectrometry): $(M+1)^+ 325$.

③ Melting point: 194°–200° C.

④ Specific rotation: $[\alpha]^{22.5}_D +84.3 \pm 1.3$ (CO.966, water).

Figure 1:
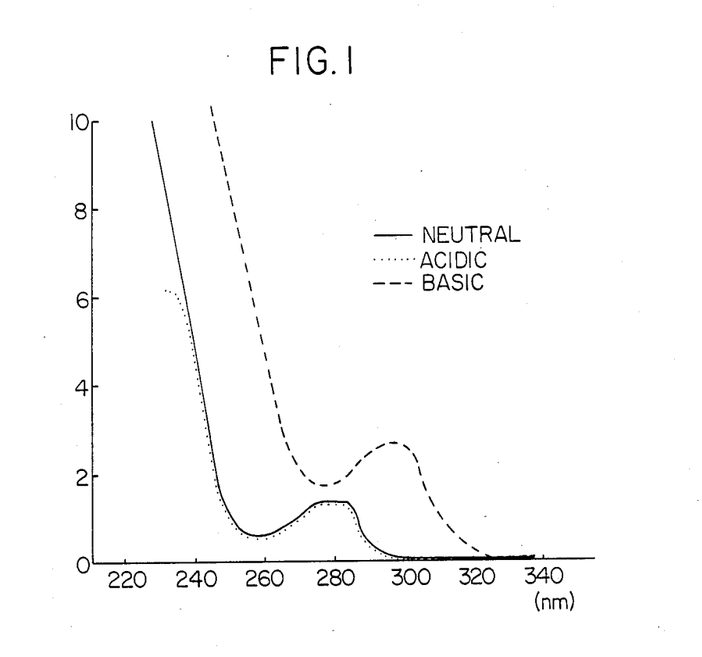
FIG. 1, FIG. 2, FIG. 3 and FIG. 4 show UV absorption spectrum in an aqueous solution, IR absorption spectrum in a potassium bromide tablet, $^1$H-NMR spectrum and $^{13}$C-NMR spectrum of Do-248-A, respectively.

⑤ UV (see FIG. 1):
$\lambda_{max}^{H2O}$ nm ($E_1{}_{cm}^{1\%}$) 276 (36);
$\lambda_{max}^{H2O+1NHCl\ 1drop}$nm ($E_1{}_{cm}^{1\%}$) 283 (36);
$\lambda_{max}^{H2O+1NNaOH\ 1drop}$nm ($E_1{}_{cm}^{1\%}$) 297 (74).

Figure 2:
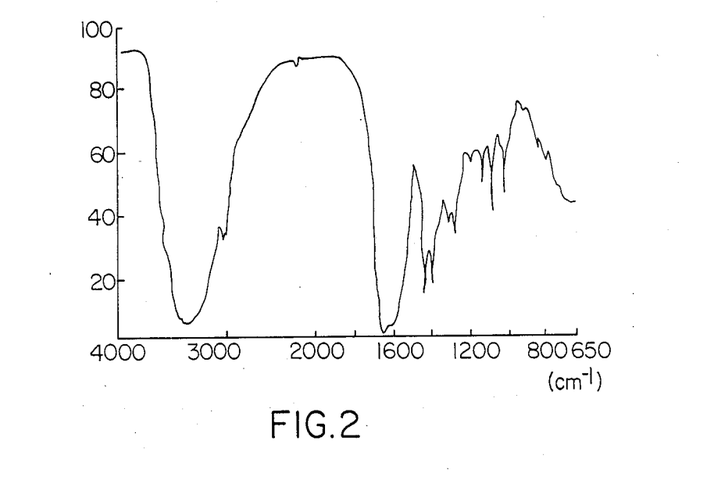

⑥ IR (see FIG. 2): $\nu_{max}^{KBr}$cm$^{-1}$ 3350, 1660, 1605, 1433, 1390, 1305, 1280, 1130, 1080, 1015, 823, 803.

⑦ Solubility: soluble in water, readily soluble in methanol, ethanol and dimethylformamide, slightly soluble in chloroform, ethylacetate and acetone, insoluble in benzene, ether and hexane.

⑧ Color reaction: Sakaguchi's reaction; positive.

⑨ Appearance and distinction between base, acid and neutral
colorless powder, amphoteric.

Figure 3:
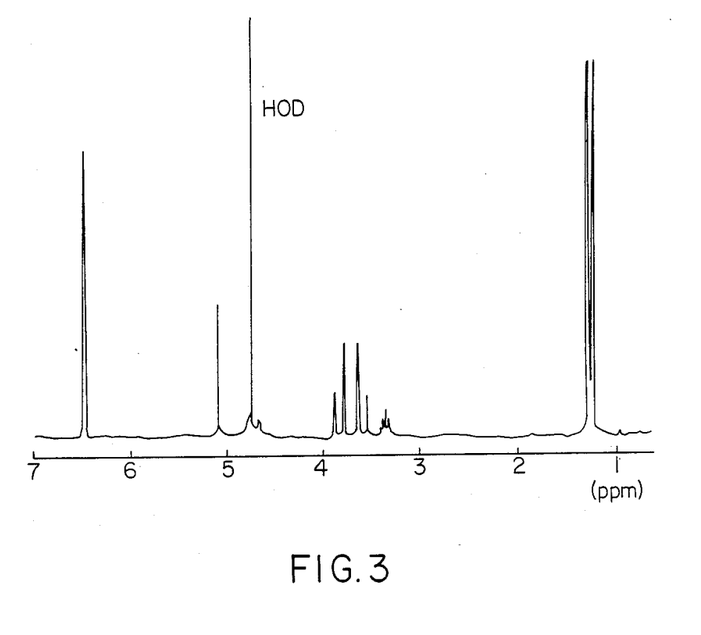

⑩ $^1$H-NMR [200 MHz.D$_2$O, external reference TMS (δ value from DSS; 0.65)] (see FIG. 3):
$\delta_{ppm}$(J=Hz) 1.23(d 6H J=7), 3.35(m 1H J=7), 3.61(AB d 1H J=17), 3.83(AB d 1H J=17), 5.10(s 1H), 6.48(s 2H).

Figure 4:
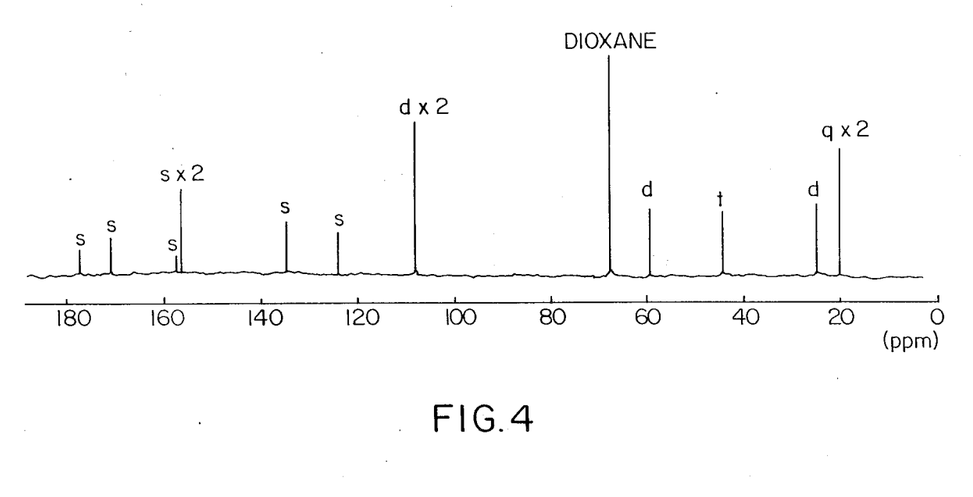

⑪ $^{13}$C-NMR (δ value 67.4) (see FIG. 4): $\delta_{ppm}$ 20.5(q×2), 25.0(d), 44.4(t), 59.3(d), 108.1(d×2), 123.8(s), 134.8(s), 156.4(s×2), 157.3(s), 171.0(s), 177.0(s).

⑫ Amino acid analysis: Glycine and ammonia were detected.

(2)

DO-248-B

① Elemental analysis: Calcd. (%); for $C_{13}H_{18}N_4O_5.2H_2O$, C 45.08, H 6.40, N 16.18. Found (%); C 45.26, H 6.13, N 16.13.

② Molecular weight (by secondary ion mass spectrometry): $(M+1)^+ 311$.

③ Melting point: 189°–193° C.

Figure 5:
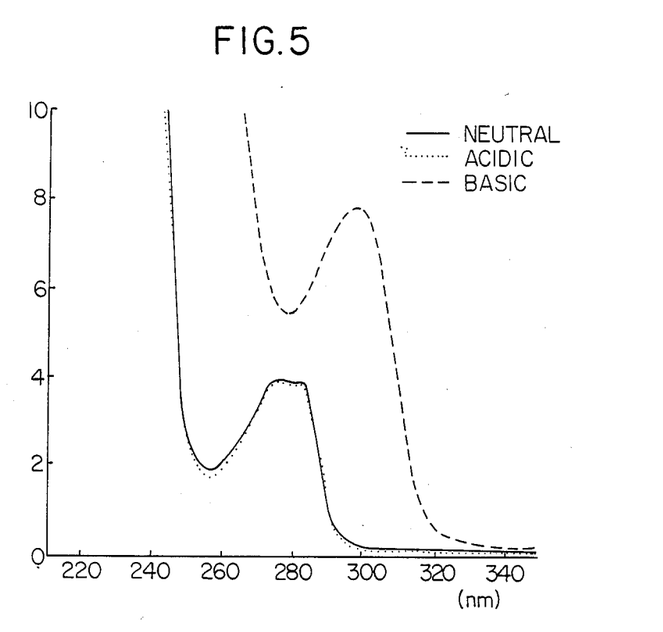
FIG. 5, FIG. 6, FIG. 7 and FIG. 8 show UV absorption spectrum in an aqueous solution, IR absorption spectrum in a potassium bromide tablet, $^1$H-NMR spectrum and $^{13}$C-NMR spectrum of DO-248-B, respectively.

④ UV (see FIG. 5):
$\lambda_{max}^{H2O}$nm ($E_1{}_{cm}^{1\%}$) 276 (36), 281.5 (36);
$\lambda_{max}^{H2O+1NHCl\ 1drop}$nm ($E_1{}_{cm}^{1\%}$) 276 (36), 281.5 (36);
$\lambda_{max}^{H2O+1NNaOH\ 1drop}$nm ($E_1{}_{cm}^{1\%}$) 297 (72).

Figure 6:
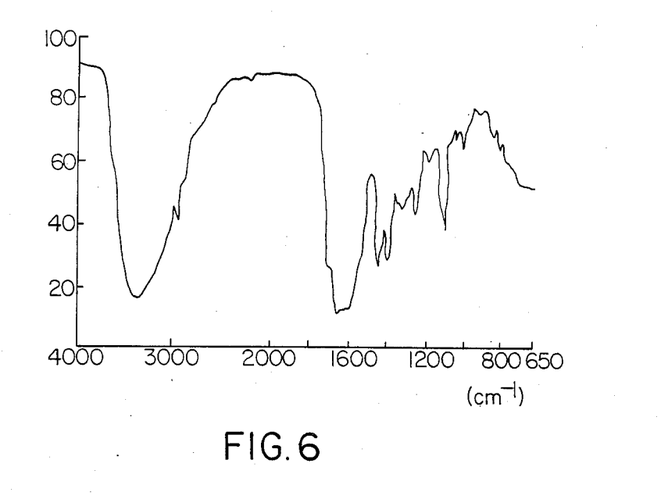

⑤ IR (see FIG. 6): $\nu_{max}^{KBr}$cm$^{-1}$ 3350, 1660, 1608, 1435, 1393, 1310, 1250, 1105, 1000.

⑥ Color reaction: Sakaguchi's reaction; positive.

⑦ Appearance and distinction between base, acid and neutral
colorless powder, amphoteric.

Figure 7:
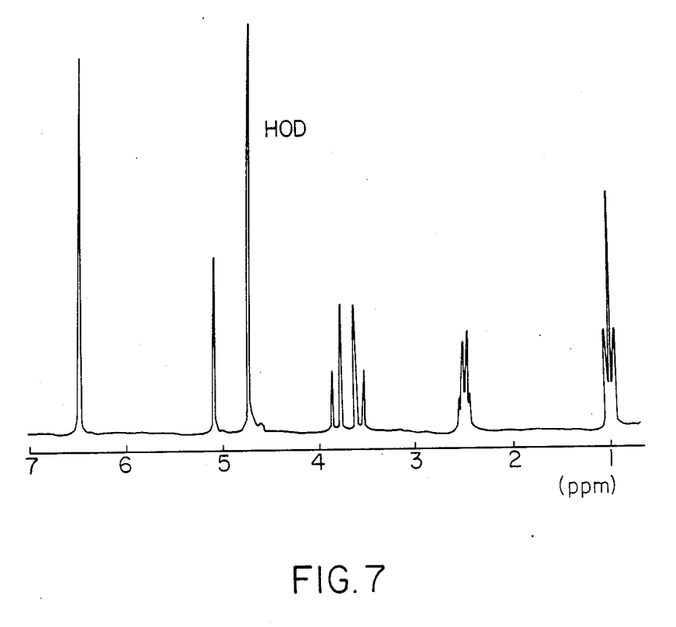

⑧ $^1$H-NMR [200 MHz.D$_2$O, external reference TMS (δ value from DSS; 0.65)] (see FIG. 7):

$\delta_{ppm}$(J=Hz) 1.00(t 3H J=7.3), 2.52(q 2H J=7.3), 3.61(AB d 1H J=17), 3.83(AB d 1H J=17), 5.10(s 1H), 6.50(s 2H).

Figure 8:
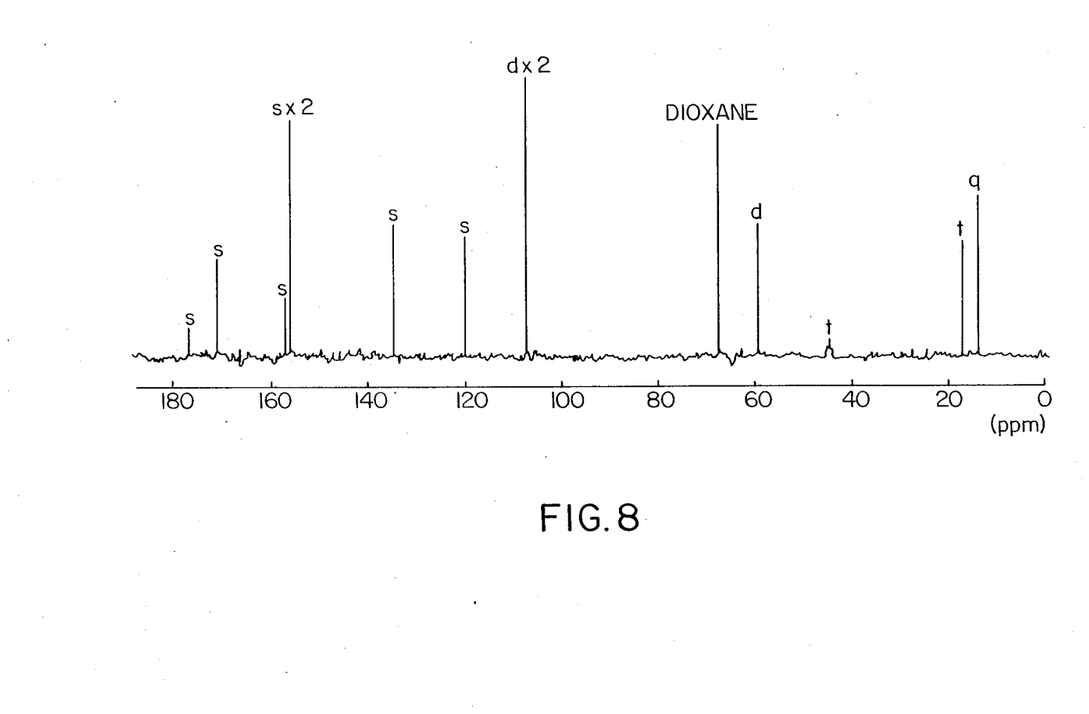

⑨ $^{13}$C-NMR [25.2 MHz, D$_2$O, internal reference dioxane (δ value 67.4)]: $\delta_{ppm}$ (J=Hz) 13.6(q), 16.9(t), 44.5(t), 59.4(d), 107.4(d×2), 120.1(s), 134.8(s), 156.0(s×2), 157.3 (s), 171.0(s), 177.0(s) (see FIG. 8).

Through the above physiochemical properties the chemical structures of DO-248-A and DO-248-B were determined to be the following Formula I.

(wherein R is ethyl or isopropyl)

Namely, DO-248-A is N-(α-guanidino-3,5-dihydroxy-4-isopropylphenylacetyl)glycine of Formula I wherein R is isopropyl and DO-248-B is N-(α-guanidino-3,5-dihydroxy-4-ethylphenylacetyl)glycine of Formula I wherein R is ethyl. Thus, DO-248-A and B are concluded to be novel antibiotics.

DO-248-A and DO-248-B are produced by a strain belonging to Streptoverticillium isolated from a soil sample in accordance with a usual method. The microorganism was identified to be the same species as *Streptoverticillium roseoverticillatum* (shinobu) Forina and Locci from an investigation for classification.

Taxonomical properties of the microorganism are as follows.

(1) Morphological property (incubated in yeast extract-malt extract agar medium at 28° C. for 14 days)

This microorganism grows well and forms lots of aerial mycelia, to which conidia adhere. Under a microscope the aerial mycelia branching into a whorl are observed, and the forms of spore chains are straight and the number of conidium per chain is mostly below 10. Under an electron microscope the surface of the conidium is smooth. Any sporangium, flagellated spore and sclerotium are not observed.

(2) Cultural characteristics

TABLE 1

| Medium | Growth | Aerial mycelium formation | color | Substrate mycelium | Soluble pigment |
|---|---|---|---|---|---|
| Sucrose nitrate agar medium | Good | Good | Pink | None to pink | None |
| Glucose asparagine agar medium | Good | Good | Pink to pale pink | Light red | None |
| Glycerol asparagine agar medium | Good | Good | Pink | Pale red | None |
| Inorganic salt starch agar medium | Good | Good | Pinkish white to pale pink | Dull red | None |
| Tyrosine agar medium | Good | Good | Pale pink to pink | Dull red | Brownish black (trace) |
| Nutrition agar medium | Good | None | — | Grayish brown | Grayish brown |
| Yeast extract-malt extract agar medium | Good | Good | Pale pink to pale brown | Reddish orange | Yellowish brown |
| Oatmeal agar medium | Good | Good | Pale pink to pale brown | Light red | None |
| Bennet's agar medium | Good | Good | Pale pink to pale orange | Dark reddish orange | Yellowish brown (trace) |

Colors are from GUIDE TO COLOUR STANDARD (Japan Color Institute).

(3) Physiological properties
Gelatin liquifaction: negative;
Melanin production: positive;
Tyrosinase reaction: weakly positive;
Coagulation of milk: negative;
Peptonization of milk: weakly positive;
Starch hydrolysis: positive.

(4) Utilization of carbohydrates

| Kind of carbohydrates | Growth |
|---|---|
| L-arabinose | + |
| D-xylose | + |
| D-glucose | ++ |
| D-fructose | ++ |
| Sucrose | + |
| Inositol | ++ |
| L-rhamnose | + |
| Raffinose | + |
| D-mannitol | ++ |
| Control (without sugar) | + |

++: Good growth
+: Fair growth

The microorganism is confirmed to grow fairly in the control (without sugar).

(5) Growth temperature
The microorganism grows at 14°–45° C. and the optimum growth temperature is 26° C. to 32° C.

(6) Composition of the cell wall
The diaminopimelic acid in LL-type was detected.
This microorganism evidently belongs to the genus Streptoverticillium deduced from several properties as above mentioned.

The closest species to the microorganism are searched for in the following literatures.
(1) Waxman S. A.: The Actinomycetes, vol. 2 (1961), (Literature 1)
(2) Elwood B. Shirling and David Gottlieb: International Journal of Systematic Bacteriology (Literature 2), vol. 18, 69–189, 279–392 (1968), vol. 19, 391–512 (1969), vol. 22, 265–394 (1972)

(3) Bergey's Manual of Determinative Bacteriology, the eighth edition (1974), (Literature 3)
(4) Other literatures refering to new species of actinomycetes As a result, the following 3 species are recognized as the closest species.
(1) *Streptoverticillium hiroshimense* (Literature 2, vol. 18, 130-134 (1968); Literature 3, 835)
(2) *Streptoverticillium roseoverticillatum* (Literature 2, vol. 18, 168 (1968); Literature 3, 834)
(3) *Streptoverticillium biverticillatus* (Literature 2, vol. 18, 300 (1968); Literature 3, 834)

The microorganism is examined and compared with the above 3 species. As the result it has been found that the microorganism is similar to the above 3 species and is most similar to *Streptoverticillium roseoverticillatum* because both have the same properties except for coagulation of milk. Accordingly, the strain DO-248 was identified to be a strain belonging to the species and named *Streptoverticillium roseoverticillatum* DO-248. This strain had been deposited as FERM 7561 since Mar. 26, 1984 in the Fermentation Research Institute Agency of the Industrial Science & Technology at Yatabe-machi, Tsukuba-gun, Ibaraki Pref. Japan and has been transfered to the deposit under Budapest Treaty with accession No. FERM BP-745 since Mar. 22, 1985.

This invention involves every process for preparing DO-248-A and/or DO-248-B by antibiotics DO-248-A- and/or DO-248-B-producing microorganisms belonging to the genus Streptoverticillium including the above DO-248 strain.

The process for preparing DO-248-A and/or DO-248-B by antibiotics DO-248-A- and/or DO-248-B-producing microorganisms is shown below. The process may be performed according to the general fermentation processes of antibiotics. Namely DO-248-A- and/or DO-248-B-producing microorganisms are incubated in a medium containing several nutrients under an aerobic condition. The incubating condition and composition of the medium may be the same as the one generally used in producing antibiotics. The medium contains carbon sources, nitrogen sources and inorganic salts as a general. Vitamins, precursors and so on may be further added as occasion demands. The carbon sources such as glucose, sucrose, starch, dextrin, glycerol, molasses, organic acids and the like may be employed alone or as a mixture. Nitrogen sources such as soy bean meal, corn steep liquor, meat extract, yeast extract, cottonseed powder, peptone, wheat germ, ammonium sulfate, ammonium nitrate and so on may be employed alone or as a mixture. Inorganic acids such as calcium carbonate, sodium chloride, potassium chloride, magnesium sulfate, cobalt chloride, several phosphates, etc. may be added in a medium as occasion demands.

The culture may be performed in accordance with the method generally used in preparing antibiotics. In this invention liquid culture is particularly preferable and in a mass production submerged aeration culture is preferable. Preferably, pH of the medium is about 5.5 to about 8.5, temperature of the fermentation is about 20° C. to about 40° C., more preferably about 25° C. to about 32° C. Cultivating time greatly depends on scale of the fermentation and is preferably about 20-80 hours in a large scale production.

Whenever occasion demands, an antifoamer such as vegetable oil and the like may be added before or during the fermentation.

After the cultivation is over, DO-248-A and DO-248-B may be isolated and recovered from the culture medium according to the general method. For example, that may be performed by filtration, centrifugation, adsorption and desorption and chromatography using several active adsorbents, extraction using several organic solvents and their combinations as occasion demands.

DO-248-A and B provided by this invention are effective on fast-acid bacteria including tubercle bacillus. A result of an antibacterial activity test of DO-248-A is shown as follows.

METHOD OF THE TEST

Fast-acid bacillus (0.01 mg) shown in Table 1 was inoculated into 2.0 ml of Dubos Tween albumin liquid medium and the minimal inhibitory concentration (MIC, μg/ml) of DO-248-A (Compound A), kanamycin (KM) and rifampicin (RFP) was measured by two-fold dilution method. The incubation temperature for *Mycobacterium marinum* was 28° C. and that for all other microorganisms was 37° C. The judgement was made generally 2 weeks later but 1 week later on *M. furtuitum* and *M. chelonei* and 5 weeks later on *M. xenopi*.

TABLE 2

| Test Microorganism | | MIC (μg/ml) | | |
|---|---|---|---|---|
| Species | Strain | Compound A | KM | RFP |
| *M. tuberculosis* | H37Rv | 0.05 | 0.025 | <0.001 |
| " | R-15[1] | 0.10 | <0.001 | >25 |
| " | R-18[2] | 0.025 | >25 | >25 |
| *M. bovis* | BCG | 0.05 | 0.00156 | <0.001 |
| *M. kansasii* | KMC1101 | 0.00313 | 6.25 | 0.0125 |
| *M. marinum* | KMC1202 | 12.5 | 3.13 | 1.56 |
| *M. scrofulaceum* | KMC2102 | 0.2 | 0.0125 | 0.00313 |
| *M. gordonae* | KMC2201 | 0.00625 | 0.39 | 0.0125 |
| *M. szulgai* | KMC2401 | 3.13 | 1.56 | 0.025 |
| *M. xenopi* | KMC2301 | 0.39 | 0.10 | 0.00625 |
| *M. simiae* | KMC1302 | 6.25 | 12.5 | >25 |
| *M. avium* | KMC3101 | 0.78 | 3.13 | 0.20 |
| *M. intracellulare* | KMC3209 | 0.025 | 0.05 | <0.001 |
| *M. nonchromogenicum* | KMC3602 | 12.5 | >25 | 25 |
| *M. fortuitum* | KMC4101 | >25 | 25 | 3.13 |
| *M. chelonei* | KMC4201 | >25 | >25 | 6.25 |
| *M. avium-intracellulare* | clinical isolated strain 16 | 0.10 | 6.25 | 3.13 |

[1]Rifanpicin resistant strain
[2]Kanamycin and rifanpicin resistant strain

As shown in Table 2, the antibiotic DO-248-A of this invention is effective against kanamycin-resistant strains and rifanpicin-resistant ones and more effective against *M. aviumintracellulare*, a causative microorganism of refractory atypical fast-acid disease, than kanamycin and rifanpicin. DO-248-B is as effective as DO-248-A. Accordingly, these antibiotics and their pharmaceutically acceptable salts can be used as active ingredients of drugs for fast-acid bacteria for human beings and animal.

DO-248-A, DO-248-B, or their pharmaceutically acceptable salts are orally or parenterally administered to human beings or animal. They can be orally administered as tablets, capsules, powders, liquids and so on formulated by common pharmaceutically acceptable excipients, stabilizers, preservatives, wetting agents, surfactants, flavors, fragrances and so on, and parenterally as injections, suppositories and the like. The dosage is considerably varied depending on condition of disease, sex, age, weight, etc. but about 0.2 to about 8 g/day are preferable for a normal adult. The anti-fast-acid drug of this invention may be administered together with other anti-fast-acid drugs in the same manner as generally practised.

Examples of preparing the desired materials of this invention, DO-248-A and DO-248-B, are shown as follows but it should not be understood to restrict this invention.

EXAMPLE 1

(a)

Fermentation step

S medium: 0.5% soluble starch, 0.5% glucose, 0.5% polypeptone, 0.5% meat extract, 0.25% yeast extract, 0.25% sodium chloride, deionized water (pH 7.0 before sterilization)

X medium: 2.0% raw starch, 2.0% glucose, 2.0% defatted soy bean powder, 0.5% yeast extract, 0.25% sodium chloride, 0.35% calcium carbonate, 0.0005% manganese dichloride tetrahydrate, 0.0005% cupper sulfate pentahydrate, 0.0005% zinc sulfate heptahydrate One platinum loop of *Streptoverticillium roseoverticillatum* DO-248 strain (FERM BP-745) was inoculated into a 500 ml-Sakaguchi's flask in which 100 ml of the above S medium was charged and cultured at 28° C. for 48 hours with shaking. Each 4 ml portions of this medium was inoculated into 500 ml-Sakaguchi's flasks charged with 100 ml of the above X medium and cultured at 28° C. for 4 days with shaking to give 43.8 L of the cultured medium.

(b)

Isolation step

To 43.8 L of the cultured medium provided in the above step was added 1.2 kg of a filter aid, Hyflo Super Cel ® (Jhons-Manville Sales Corp.) and the cells were filtered out. The filtrate (39 L) was passed through a column with 4.36 L of a synthetic adsorbent HP-20 (150–300 μm, Mitsubishi Chemical Industries Co., Ltd.) to absorb the desired ingredient. The column was washed with water and eluted with methanol to give active fractions, which were concentrated under reduced pressure. The active fractions in the first half contaminated with many water soluble impurities were subjected to column chromatography with 580 ml of a synthetic adsorbent CHP-20P (75–150 μm, Mitsubishi Chemical Industries Co., Ltd.), the resulting active fractions were combined and lyophilized to yield 25 g of a brown crude powder. Then, 25 g of this crude powder is adsorbed to a column with 470 g of silicagel (63–200 μm, Merck & Co.) and eluted with chloroform-:methanol:water (15:10:1) to remove impurities and then with methanol to elute the active ingredient. The active fractions were evaporated to dryness in vacuo. Into a small amount of water was dissolved 3.18 g of the resulting yellowish brown residue containing the active ingredient and passed through a column of 700 ml of Sephadex LH-20 (Pharmacia AB). The column was washed with water and eluted with methanol. The eluate was evaporated to dryness in vacuo. The resulting power (1.22 g) is dissolved again in a small amount of water and passed through a column with Toyopearl HW-50C (100–500 μm, Toyo Soda Mfg. Co., Ltd.) to absorb the active ingredient. The column was washed with water and then eluted with methanol. The active fractions were evaporated to dryness in vacuo (according to this purification impurities are not removed completely, but DO-248-B, the minor component, was collected in a fair amount from the first half fractions.). Each crude powders were combined and passed through reverse phase Lobar ® column (Lichroprep RP-18 ®, 40–63 μm, 25×310 mm, Merck & Co.) with methanol-water (1:1) to remove impurities and resulting active fractions were evaporated to dryness in vacuo to provide 445 mg of yellow powder. At last the resultant was separated to DO-248-A and DO-248-B by reverse phase high performance liquid chromatography with semi-collection column, Nucleosil ® 10C$_8$ (10×250 mm, M. Nargel Co., Ltd.), (it takes 14–15 minutes and 7–8 minutes to elute DO-248-A and DO-248-B, respectively, with methanol-water (1:2) at the flow rate of 3 ml/minute. A UV 254 nm detector was employed.). The eluates were then lyophilized to yield 116 mg and 16 mg of colorless powder of DO-248-A and DO-248-B, respectively.

EXAMPLE 2

(a)

Fermentation step

S medium: 0.5% soluble starch, 0.5% glucose, 0.5% polypeptone, 0.5% meat extract, 0.25% yeast extract, 0.25% sodium chloride, deionized water (pH 7.0 before sterilization).

A medium: 2% raw starch, 2% glucose, 2% defatted soy bean powder, 1% Bactosoyton (Trade name), 0.25% sodium chloride, water (pH 7.0 before sterilization).

To a 2 L Erlenmeyer flask charged with 800 ml of S medium consisting of the above composition was inoculated a seeding culture of *Streptoverticillium roseoverticillatum* DO-248 (FERM BP-745) on slant and incubated at 28° C. for 24 hours with shaking of 180 r.p.m.

Into 30 L jars charged with 20 L of A medium consisting of the above composition was planted each 800 ml portions of this culture medium and incubated with 20 L/minute aeration and 180–300 r.p.m. at 28° C. for 5 days.

(b)

Isolation step

The culture medium provided in the above step was adjusted to pH 3.0 and centrifuged by Scharples type centrifuge to give 100 L of the supernatant. The supernatant was passed through a column of 10 L of Dowex® 50×4 (NH$_4$+ type) (U.S., Dow Chemical Co.) at a flow rate of 700 ml/minute. After washing with water, the column was eluted with 0.3N aqueous ammonia to give 35 L of active fractions. After ammonia was removed, the fractions were adjusted to pH 9.0 and passed through a column of 5 L of Dowex 1×2 (Cl$^-$ type) at the flow rate of 150 ml/minute. The column was eluted with 50% methanol containing 5% sodium chloride and 13 L of the resulting active fractions were evaporated in vacuo. The residual solution was adjusted to pH 7.0 and passed through a column of 2.5 L of HP-20 (Mitsubishi Chemical Industries Co., Ltd.). After washing with water, the column was eluted with 50% methanol and 2.7 L of the active fractions were evaporated. The resultant was lyophilized to yield 2.25 g of crude powder of DO-248.

(b)

Purification step of DO-248 A

Detection and quantitation of DO-248-A in the following purification step were performed with high performance liquid chromatography tracing absorbance at 230 nm, employing a column (4×250 nm) of Nucleosil® 10C$_8$ (M. Nargel Co., Ltd.) and a mixture of 20 mM phosphate buffer (pH 7.0) and acetonitrile (5:1). Under the condition a retention volume of DO-248-A was 8.00 ml.

The crude powder (2.0 g) provided in the above step (containing about 105 mg of DO-248-A) was dissolved in about 40 ml of 20 mM phosphate buffer (pH 7.0). After removing a small amount of impurities, this solution was subjected on a column (200 ml) of QAE-Sephadex A-25 (Pharmacia AB). After 200 ml of 20 mM phosphate buffer (pH 7.0) passed through the column, a linear concentration gradient elution was performed with 600 ml of the same buffer and 600 ml of the same containing 1M sodium chloride. The eluting solution was traced with the above high performance liquid chromatography to give fractions containing DO-248-A. The collected eluates were applied to a column (100 ml) of CHP-20P (Mitsubishi Chemical Industries Co., Ltd.). The column was washed with water and then a linear concentration gradient elution was performed with 300 ml of water and 300 ml of 80% methanol. The eluting solution was traced with high performance liquid chromatography to give fractions containing DO-248-A. The collected eluates were evaporated in vacuo and then lyophilized to yield 100 mg of powder whose purity was about 70%. About 50 mg portions of this powder was subjected to a high performance liquid chromatography collection column (Nucleosil® 30C$_{18}$, 20 ×250 mm) at one time and developed with a mixture of 50 mM phosphate buffer (pH 7.0) and methanol (9:1). The fractions were traced through absorbance at 230 nm and those fractions containing the desired substance in a peak were collected. This collected solution was passed through a column (40 ml) of CHP-20P and the column was washed with water and eluted with 50% methanol and the eluates containing DO-248-A were collected by detecting with the above high performance liquid chromatography, evaporated in vacuo and then lyophilized to give 60 mg of a colorless powder of DO-248-A.

What we claim is:

1. A compound of Formula I;

wherein R is ethyl or isopropyl, and the pharmaceutically acceptable salt thereof.

2. The compound of claim 1 wherein R is isopropyl, antibiotic DO-248-A.

3. The compound of claim 1 wherein R is ethyl, antibiotic DO-248-B.